United States Patent
Huang et al.

(10) Patent No.: US 10,535,203 B2
(45) Date of Patent: Jan. 14, 2020

(54) DIGITAL DENTAL MESH SEGMENTATION METHOD AND DIGITAL DENTAL MESH SEGMENTATION DEVICE

(71) Applicant: Candor Ltd., Taichung (TW)

(72) Inventors: Chien-Chih Huang, Taoyuan (TW); Cheng-Han Wu, Taichung (TW); Wen-Pin Hsu, New Taipei (TW); Ting-Hui Kao, Changhua County (TW); Chih-Hao Hsu, Kaohsiung (TW); Hsuan-Hung Liu, Hsinchu County (TW); Jen-How Wang, Taipei (TW); Chi-Kang Chen, Hsinchu County (TW)

(73) Assignee: Candor Ltd., Taichung (TW)

(*) Notice: Subject to any disclaimer, the term of this patent is extended or adjusted under 35 U.S.C. 154(b) by 0 days.

(21) Appl. No.: 16/198,888

(22) Filed: Nov. 23, 2018

(65) Prior Publication Data
US 2019/0156587 A1     May 23, 2019

(30) Foreign Application Priority Data
Nov. 23, 2017   (TW) .............................. 106140633 A

(51) Int. Cl.
*G06T 19/20*     (2011.01)
*A61C 7/00*      (2006.01)
(Continued)

(52) U.S. Cl.
CPC .............. *G06T 19/20* (2013.01); *A61C 7/002* (2013.01); *G06T 7/00* (2013.01); *G06T 17/20* (2013.01);
(Continued)

(58) Field of Classification Search
CPC ................................ G06T 19/20; G06T 7/00; G06T 17/20; G06T 2207/30036; A61C 7/002;
(Continued)

(56) References Cited

U.S. PATENT DOCUMENTS 6,297,799 B1 * 10/2001 Knittel ................ G06F 3/04812
345/419
6,371,761 B1 *  4/2002 Cheang .................... A61C 7/00
433/24
(Continued)

FOREIGN PATENT DOCUMENTS

| CN | 105726142 | 7/2016 |
|----|-----------|--------|
| CN | 105769353 | 7/2016 |

(Continued)

OTHER PUBLICATIONS

Kondo et al., Tooth Segmentation of Dental Study Models Using Range Images, IEEE Transactions on Medical Imaging, vol. 23, No. 3, Mar. 2004, pp. 350-362 (Year: 2004).*
(Continued)

*Primary Examiner* — Haixia Du
(74) *Attorney, Agent, or Firm* — JCIPRNET

(57) ABSTRACT

A digital dental mesh segmentation method and a digital dental mesh segmentation device are provided. The digital dental mesh segmentation method includes: receiving a digital dental mesh, including a plurality of teeth; inserting a tooth interface separator at a tooth interface of the digital dental mesh, the tooth interface separator being at a first location; receiving a three-dimensional movement signal and a three-dimensional rotation signal to move and rotate the tooth interface separator from the first location to a second location; and segmenting the digital dental mesh according to the tooth interface separator at the second location to obtain an independent digital teeth model.

14 Claims, 4 Drawing Sheets

(51) Int. Cl.
*G06T 17/20* (2006.01)
*G06T 7/00* (2017.01)

(52) U.S. Cl.
CPC ...... *G06T 2200/24* (2013.01); *G06T 2210/41* (2013.01); *G06T 2219/008* (2013.01); *G06T 2219/2004* (2013.01); *G06T 2219/2016* (2013.01)

(58) Field of Classification Search
CPC ... A61C 13/0004; A61C 9/0046; A61C 9/004; A61B 5/0088; A61B 5/4547
See application file for complete search history.

(56) References Cited

U.S. PATENT DOCUMENTS

| | | | |
|---|---|---|---|
| 7,080,979 | B2 | 7/2006 | Rubbert et al. |
| 2010/0153075 | A1 | 6/2010 | Sporbert et al. |
| 2013/0022252 | A1 | 1/2013 | Chen et al. |
| 2013/0317800 | A1 | 11/2013 | Wu et al. |
| 2013/0325431 | A1* | 12/2013 | See .............. A61C 7/002 703/11 |
| 2015/0173855 | A1 | 6/2015 | Sporbert et al. |
| 2016/0220173 | A1 | 8/2016 | Ribnick et al. |

FOREIGN PATENT DOCUMENTS

| | | |
|---|---|---|
| TW | 471960 | 1/2002 |
| TW | 476634 | 2/2002 |
| TW | 481552 | 4/2002 |
| TW | 201628567 | 8/2016 |

OTHER PUBLICATIONS

H. Akhoondali, et al., "Rapid Automatic Segmentation and Visualization of Teeth in CT-Scan Data," Journal of Applied Sciences, vol. 9, Issue 11, 2009, pp. 2031-2044.
Nonlapas Wongwaen, et al., "Computerized Algorithm for 3D Teeth Segmentation," 2010 International Conference on Electronics and Information Engineering, vol. 1, Sep. 2010, pp. 1-5.
Thomas Kronfeld, et al., "Snake-Based Segmentation of Teeth from Virtual Dental Casts," Computer-Aided Design & Applications, vol. 7, Jan. 2010, pp. 1-12.
Yokesh Kumar, et al., "Improved Segmentation of Teeth in Dental Models," Computer-Aided Design and Applications, vol. 8, Jan. 2011, pp. 1-15.
Robert Wanat, "A Problem of Automatic Segmentation of Digital Dental Panoramic X-Ray Images for Forensic Human Identification", Proceedings of CESCG 2011: The 15th Central European Seminar on Computer Graphics, 2011, pp. 1-8.
David A. Mouritsen, "Automatic Segmentation of Teeth in Digital Dental Models," Master of Science, The University of Alabama at Birmingham, 2013, pp. 1-245.
Guang Yang, et al., "A dental model segmentation algorithm for Invisalign software," Journal of Chemical and Pharmaceutical Research, vol. 6, Jan. 2014, pp. 401-408.
Tamayo-Quintero, J. D., et al., "Image Segmentation Techniques Applied to Point Clouds of Dental Models with an improvement in Semi-Automatic Teeth Segmentation," IPCV, 2014, pp. 1-7.
Sheng-Hui Liao, et al., "Automatic Tooth Segmentation of Dental Mesh Based on Harmonic Fields," BioMed Research International, Jan. 2015, pp. 1-11.
J.D.Tamayo-Quintero, et al., "Emerging Trends in Image Processing, Computer Vision and Pattern Recognition Chapter 28—Semi-Automatic teeth segmentation in 3D models of dental casts using a hybrid methodology," Elsevier Inc., 2015, pp. 1-2.
Zhongyi Li, et al., "Interactive Tooth Separation from Dental Model Using Segmentation Field," PLoS One, vol. 11, No. 8, Aug. 17, 2016, pp. 1-16.

* cited by examiner

DIGITAL DENTAL MESH SEGMENTATION METHOD AND DIGITAL DENTAL MESH SEGMENTATION DEVICE

CROSS-REFERENCE TO RELATED APPLICATION

This application claims the priority benefit of Taiwan application serial no. 106140633, filed on Nov. 23, 2017. The entirety of the above-mentioned patent application is hereby incorporated by reference herein and made a part of this specification.

BACKGROUND OF THE INVENTION

Field of the Invention

The invention relates to a digital dental mesh segmentation method and a digital dental mesh segmentation device, and particularly relates to a digital dental mesh segmentation method and a digital dental mesh segmentation device for performing dental mesh segmentation by using a missing tooth mark, a center line mark, an optimal arch-form crossline point (OACP) mark, and a tooth interface separator.

Description of Related Art

Because of people's desire for beautiful teeth, dental orthodontics has been an important business for dentists. The general orthodontics uses traditional metal braces. Such metal braces can only be removed after the treatment process is over and may easily cause oral injury, allergy, and other problems and thus make it difficult to maintain oral health. Therefore, invisible braces have been proposed.

Before making invisible braces, the dentist needs to obtain the patient's digital dental mesh first, segment the digital dental mesh into multiple independent tooth models, and arrange the digital tooth models that can be independently moved and rotated into the expected result, and then print out the result as a physical dental mesh for making the invisible braces. A technician is required in order to use computer software to segment the digital dental mesh to obtain the independent tooth models, which takes a lot of efforts and time. Therefore, it is an important issue for technicians in the field to design simple operation method and platform for the dentist to complete digital dental mesh segmentation with high accuracy in a short period of time.

SUMMARY OF THE INVENTION

The invention provides a digital dental mesh segmentation method and a digital dental mesh segmentation device for ordinary people to complete digital dental mesh segmentation with high accuracy in a short period of time.

A digital dental mesh segmentation method according to an embodiment of the invention includes: receiving a digital dental mesh that includes a plurality of teeth. The digital dental mesh segmentation method includes inserting a tooth interface separator at a tooth interface of the digital dental mash, wherein the tooth interface separator is at a first location. The digital dental mesh segmentation method includes receiving a three-dimensional movement signal and a three-dimensional rotation signal to move and rotate the tooth interface separator from the first location to a second location. The digital dental mesh segmentation method includes segmenting the digital dental mesh according to the tooth interface separator at the second location.

In an embodiment of the invention, the digital dental mesh segmentation method further includes: receiving a first signal to mark a missing tooth of the digital dental mesh before inserting the tooth interface separator at the tooth interface of the digital dental mesh.

In an embodiment of the invention, the digital dental mesh segmentation method further includes: receiving a second signal to mark a center line of the digital dental mesh before inserting the tooth interface separator at the tooth interface of the digital dental mesh.

In an embodiment of the invention, the digital dental mesh segmentation method further includes: receiving a third signal to mark an optimal arch-form crossline point (OACP) of the digital dental mesh before inserting the tooth interface separator at the tooth interface of the digital dental mesh.

In an embodiment of the invention, the digital dental mesh segmentation method further includes: deleting gums of the digital dental mesh that has been segmented to obtain the teeth that have been segmented.

In an embodiment of the invention, the digital dental mesh segmentation method further includes: generating a three-axis indication line on the tooth interface separator when the tooth interface separator receives a selection operation, wherein a first indication line and a second indication line of the three-axis indication line are parallel to the tooth interface separator, the first indication line is perpendicular to the second indication line, and a third indication line of the three-axis indication line is perpendicular to the tooth interface separator.

In an embodiment of the invention, the digital dental mesh segmentation method further includes: displaying a first plane that includes the first indication line and the third indication line with a first color, and displaying a second plane that includes the second indication line and the third indication line with a second color.

In an embodiment of the invention, the first plane and the second plane are translucent.

A digital dental mesh segmentation device according to an embodiment of the invention includes a processor and a memory. The memory is coupled to the processor. The memory stores a digital dental mesh. The processor receives the digital dental mesh that includes a plurality of teeth. The processor inserts a tooth interface separator at a tooth interface of the digital dental mash, wherein the tooth interface separator is at a first location. The processor receives a three-dimensional movement signal and a three-dimensional rotation signal to move and rotate the tooth interface separator from the first location to a second location. The processor segments the digital dental mesh according to the tooth interface separator at the second location.

In an embodiment of the invention, the processor receives a first signal to mark a missing tooth of the digital dental mesh.

In an embodiment of the invention, the processor receives a second signal to mark a center line of the digital dental mesh.

In an embodiment of the invention, the processor receives a third signal to mark an optimal arch-form crossline point of the digital dental mesh.

In an embodiment of the invention, the processor deletes gums of the digital dental mesh that has been segmented to obtain the teeth that have been segmented.

In an embodiment of the invention, the processor generates a three-axis indication line on the tooth interface separator when the tooth interface separator receives a selection operation, wherein a first indication line and a second indication line of the three-axis indication line are parallel to the tooth interface separator, the first indication line is perpendicular to the second indication line, and a third indication line of the three-axis indication line is perpendicular to the tooth interface separator.

In an embodiment of the invention, the processor displays a first plane that includes the first indication line and the third indication line with a first color, and displays a second plane that includes the second indication line and the third indication line with a second color.

In an embodiment of the invention, the first plane and the second plane are translucent.

Based on the above, in the digital dental mesh segmentation method and the digital dental mesh segmentation device according to one or some embodiments of the invention, the digital dental mesh is received and the tooth interface separator is inserted at the tooth interface of the digital dental mesh, and the tooth interface separator is moved and rotated from the original first location to the second location according to the three-dimensional movement signal and the three-dimensional rotation signal, and then the digital dental mesh is segmented according to the tooth interface separator at the second location. The digital dental mesh segmentation process described above allows the user to complete digital dental mesh segmentation in a short period of time and obtain a highly accurate segmentation result.

To make the aforementioned and other features and advantages of the invention more comprehensible, several embodiments accompanied with drawings are described in detail as follows.

BRIEF DESCRIPTION OF THE DRAWINGS

The accompanying drawings are included to provide a further understanding of the invention, and are incorporated in and constitute a part of this specification. The drawings illustrate exemplary embodiments of the invention and, together with the description, serve to explain the principles of the invention.

DESCRIPTION OF THE EMBODIMENTS

Figure 1:
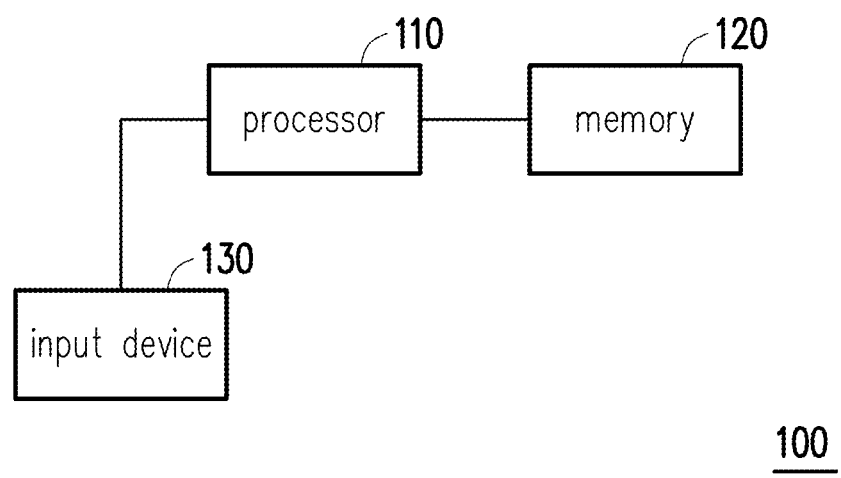
FIG. 1 is a block diagram of the digital dental mesh segmentation device according to an embodiment of the invention.

FIG. 1 is a block diagram of a digital dental mesh segmentation device according to an embodiment of the invention.

Referring to FIG. 1, a digital dental mesh segmentation device 100 of the invention includes a processor 110, a memory 120, and an input device 130. The memory 120 is coupled to the processor 110. The input device 130 is coupled to the processor 110.

The processor 110 may be a central processing unit (CPU), other programmable microprocessors for general use or special use, a digital signal processor (DSP), a programmable controller, an application specific integrated circuit (ASIC), other similar devices, or a combination of the foregoing devices, for example.

The memory 120 may be a fixed or portable random access memory (RAM) of any form, a read-only memory (ROM), a flash memory, a hard disk drive (HDD), a solid state drive (SSD), a similar device, or a combination of the foregoing devices, for example. The input device 130 may be an input component, such as a keyboard, a mouse, and so on.

In an embodiment, the digital dental mesh segmentation device 100 of the invention may include a user interface stored in the memory 120, by which the user may operate a digital dental mesh via the input device 130 to quickly and accurately segment the digital dental mesh.

Figure 2:
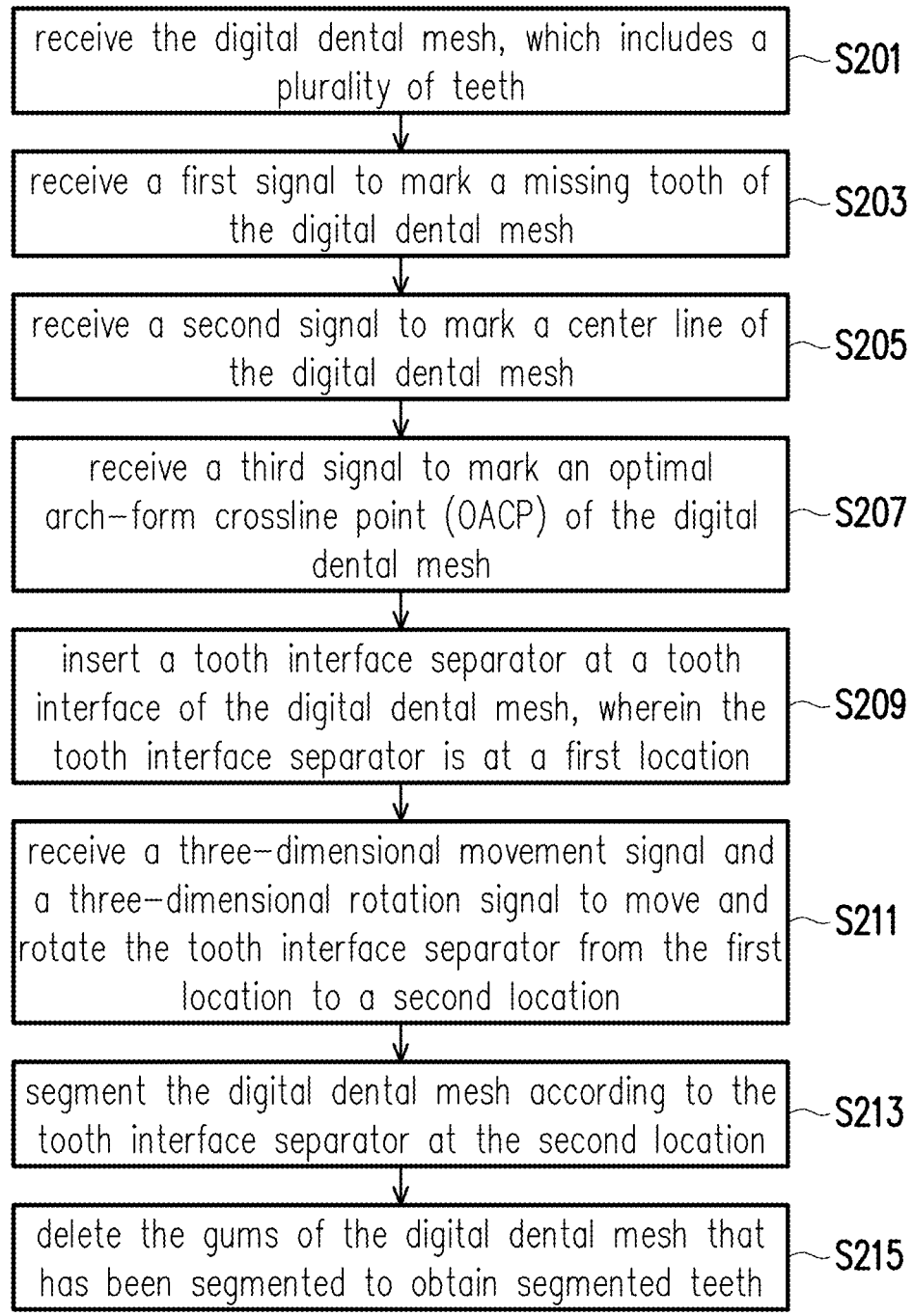
FIG. 2 is a flowchart of the digital dental mesh segmentation method according to an embodiment of the invention.
Figure 3:
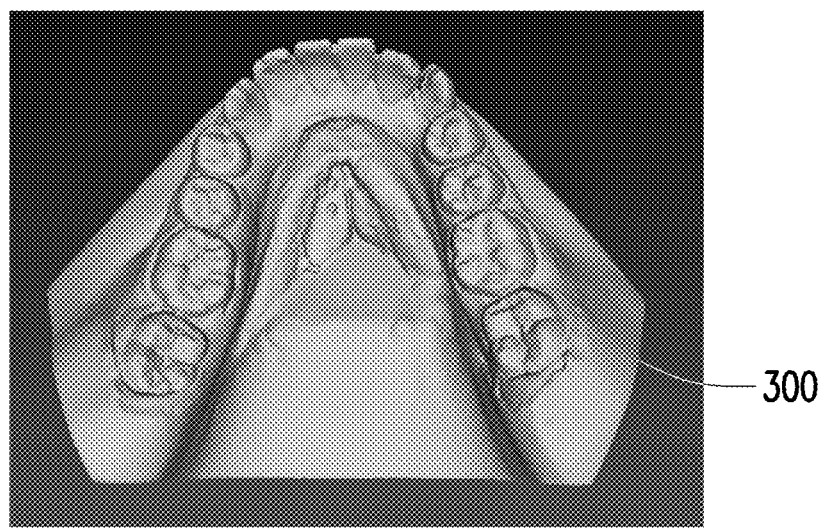
FIG. 3 is a picture of the digital dental mesh according to an embodiment of the invention.
Figure 4:
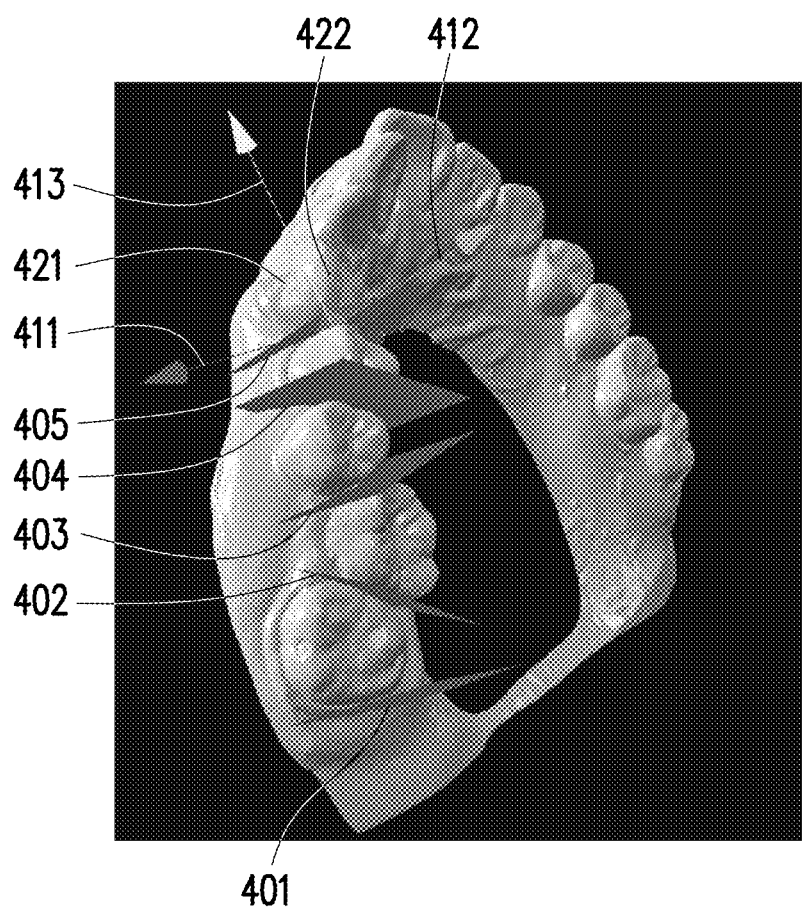
FIG. 4 is a picture of the digital dental mesh with the tooth interface separator inserted therein according to an embodiment of the invention.
Figure 5:
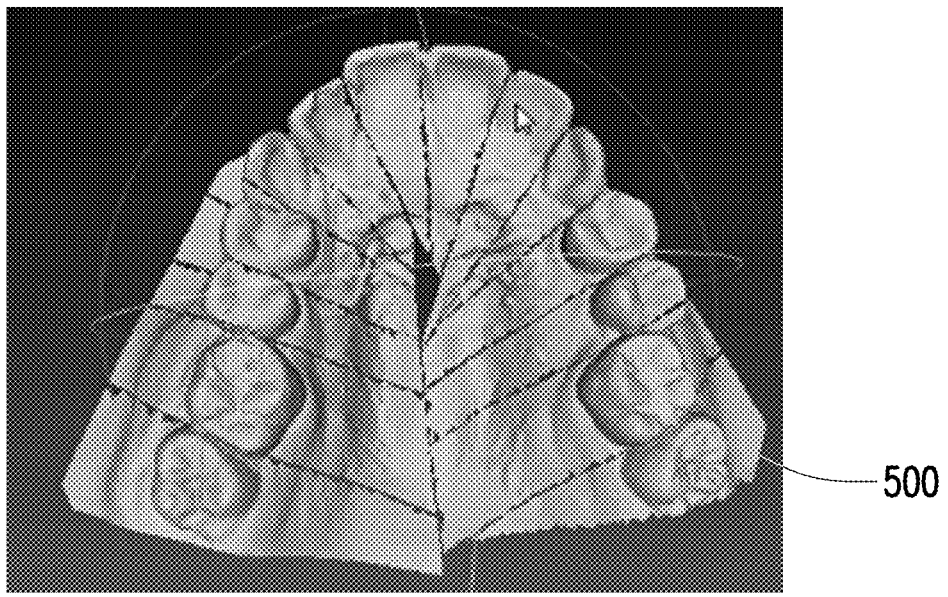
FIG. 5 is a picture of the digital dental mesh that has been segmented according to an embodiment of the invention.

FIG. 2 is a flowchart of a digital dental mesh segmentation method according to an embodiment of the invention. FIG. 3 is a picture of the digital dental mesh according to an embodiment of the invention. FIG. 4 is a picture of the digital dental mesh with a tooth interface separator inserted therein according to an embodiment of the invention. FIG. 5 is a picture of the digital dental mesh that has been segmented according to an embodiment of the invention.

Referring to FIG. 2, in Step S201, the digital dental mesh is received, which includes a plurality of teeth. As shown in FIG. 3, the processor 110 may receive data of the digital dental mesh 300, and the digital dental mesh 300 includes gums and a plurality of teeth connected with the gums. The digital dental mesh 300 may be a dental mesh for upper teeth or lower teeth.

In Step S203, a first signal is received to mark a missing tooth of the digital dental mesh. Specifically, the user may mark the missing tooth of the digital dental mesh via an operation interface of the input device 130 to increase the accuracy of dental mesh segmentation.

In Step S205, a second signal is received to mark a center line of the digital dental mesh. Specifically, the user may mark the center line of the digital dental mesh via the operation interface of the input device 130 to increase the accuracy of dental mesh segmentation.

In Step S207, a third signal is received to mark an optimal arch-form crossline point (OACP) of the digital dental mesh. Specifically, the user may mark the optimal arch-form crossline point of the digital dental mesh via the operation interface of the input device 130 to facilitate an automatic arrangement process after the dental mesh segmentation. The optimal arch-form crossline point is for creating an optimal arch-form crossline. The optimal arch-form crossline refers to a straight line formed between a lower left point and an upper right point of a tooth FDI (Fédération Dentaire Internationale) No. 16 and a straight line formed between a lower right point and an upper left point of a tooth FDI No. 26.

In Step S209, a tooth interface separator is inserted at a tooth interface of the digital dental mesh and is at a first location. Specifically, the processor 110 may approximately determine the locations of all the teeth in the aforementioned marking process, and insert the tooth interface separator at the tooth interface between all the adjacent teeth respectively. However, since there is no detailed dental mesh segmentation data in this stage, the location of the tooth interface separator does not perfectly segment adjacent two teeth.

In Step S211, a three-dimensional movement signal and a three-dimensional rotation signal are received to move and rotate the tooth interface separator from the first location to a second location. Specifically, the user may three-dimensionally move and rotate the selected tooth interface separator via the operation interface of the input device 130 to move and rotate the tooth interface separator from the original first location to the second location. The tooth interface separator at the second location may more accurately segment adjacent two teeth.

For example, in FIG. 4, the user may adjust the locations of a tooth interface separator 401, a tooth interface separator 402, a tooth interface separator 403, a tooth interface separator 404, and a tooth interface separator 405, such that all the tooth interface separators may more accurately segment adjacent two teeth. In order to facilitate the adjustment, take the tooth interface separator 405 as an example, when the tooth interface separator 405 receives a selection operation of the user, the processor 110 may generate a three-axis indication line on the tooth interface separator 405. The three-axis indication line includes a first indication line 411, a second indication line 412, and a third indication line 413. The first indication line 411 and the second indication line 412 are parallel to the tooth interface separator 405. The first indication line 411 is perpendicular to the second indication line 412. The third indication line 413 is perpendicular to the tooth interface separator 405.

In addition, the processor 110 may display a first plane 421 including the first indication line 411 and the third indication line 413 with a first color and display a second plane 422 including the second indication line 412 and the third indication line 413 with a second color. In an embodiment, the first plane 421 and the second plane 422 are translucent to allow the user to more accurately move and rotate the tooth interface separator 405 by using the first plane 421 and the second plane 422.

In Step S213, the digital dental mesh is segmented according to the tooth interface separator at the second location. As shown in FIG. 5, after determining the locations of all the tooth interface separators, the processor 110 may segment the digital dental mesh 300 according to the locations of all the tooth interface separators to generate a digital dental mesh 500 that has been segmented.

In Step S215, the gums of the digital dental mesh that has been segmented is deleted to obtain segmented teeth. Specifically, after generating the digital dental mesh 500 that has been segmented, the processor 110 may automatically delete the gums of the digital dental mesh 500 that has been segmented to obtain the segmented teeth, that is, an independent digital teeth model.

By the digital dental mesh segmentation method as described above, even an untrained person may complete digital dental mesh segmentation with high accuracy in a short period of time (e.g., 30 minutes) by using the operation interface of the invention. Thus, when a digital dental mesh needs to be segmented, it is not required to hire a professional technician to spend several days to perform digital dental mesh segmentation by computer software. Therefore, the efficiency of orthodontic procedures is improved.

To sum up, in the digital dental mesh segmentation method and the digital dental mesh segmentation device according to one or some embodiments of the invention, the digital dental mesh is received and the tooth interface separator is inserted at the tooth interface, and the tooth interface separator is moved and rotated from the original first location to the second location according to the three-dimensional movement signal and the three-dimensional rotation signal, and then the digital dental mesh is segmented according to the tooth interface separator at the second location. The digital dental mesh segmentation process described above allows the user to complete dental mesh segmentation in a short period of time and obtain a highly accurate segmentation result.

It will be apparent to those skilled in the art that various modifications and variations can be made to the disclosed embodiments without departing from the scope or spirit of this invention. In view of the foregoing, it is intended that the invention covers modifications and variations provided that they fall within the scope of the following claims and their equivalents.

What is claimed is:

1. A digital dental mesh segmentation method, comprising:
   receiving a user interface and a digital dental mesh, the digital dental mesh comprising a plurality of teeth;
   displaying the digital dental mesh on the user interface;
   receiving, through operation of the input device by a user on the user interface, an optimal arch-form crossline point of the digital dental mesh;
   displaying the optimal arch-form crossline point of the digital dental mesh on the user interface;
   inserting a tooth interface separator at a tooth interface of the digital dental mesh, wherein the tooth interface separator is at a first location;
   receiving a three-dimensional movement signal and a three-dimensional rotation signal to move and rotate the tooth interface separator from the first location to a second location; and
   segmenting the digital dental mesh according to the tooth interface separator at the second location.

2. The digital dental mesh segmentation method according to claim 1, further comprising:
   receiving a first signal to mark a missing tooth of the digital dental mesh before inserting the tooth interface separator at the tooth interface of the digital dental mesh.

3. The digital dental mesh segmentation method according to claim 1, further comprising: receiving a second signal to mark a center line of the digital dental mesh before inserting the tooth interface separator at the tooth interface of the digital dental mesh.

4. The digital dental mesh segmentation method according to claim 1, further comprising: deleting gums of the digital dental mesh that has been segmented to obtain the teeth that have been segmented.

5. The digital dental mesh segmentation method according to claim 1, further comprising: generating a three-axis indication line on the tooth interface separator when the tooth interface separator receives a selection operation, wherein a first indication line and a second indication line of the three-axis indication line are parallel to the tooth interface separator, the first indication line is perpendicular to the second indication line, and a third indication line of the three-axis indication line is perpendicular to the tooth interface separator.

6. The digital dental mesh segmentation method according to claim 5, further comprising: displaying a first plane that comprises the first indication line and the third indication line with a first color, and displaying a second plane that comprises the second indication line and the third indication line with a second color.

7. The digital dental mesh segmentation method according to claim 6, wherein the first plane and the second plane are translucent.

8. A digital dental mesh segmentation device, comprising:
a processor;
a memory coupled to the processor and storing a digital dental mesh and a user interface; and
an input device, wherein the processor:
receives the user interface and the digital dental mesh from the memory, the digital dental mesh comprising a plurality of teeth;
displays the digital mesh on the user interface;
receives, through operation of the input device by a user on the user interface, an optimal arch-form crossline point of the digital dental mesh;
displays the optimal arch-form crossline point of the digital dental mesh on the user interface;
inserts a tooth interface separator at a tooth interface of the digital dental mesh, wherein the tooth interface separator is at a first location;
receives a three-dimensional movement signal and a three-dimensional rotation signal to move and rotate the tooth interface separator from the first location to a second location; and
segments the digital dental mesh according to the tooth interface separator at the second location.

9. The digital dental mesh segmentation device according to claim 8, wherein the processor receives a first signal to mark a missing tooth of the digital dental mesh.

10. The digital dental mesh segmentation device according to claim 8, wherein the processor receives a second signal to mark a center line of the digital dental mesh.

11. The digital dental mesh segmentation device according to claim 8, wherein the processor deletes gums of the digital dental mesh that has been segmented to obtain the teeth that have been segmented.

12. The digital dental mesh segmentation device according to claim 8, wherein the processor generates a three-axis indication line on the tooth interface separator when the tooth interface separator receives a selection operation, wherein a first indication line and a second indication line of the three-axis indication line are parallel to the tooth interface separator, the first indication line is perpendicular to the second indication line, and a third indication line of the three-axis indication line is perpendicular to the tooth interface separator.

13. The digital dental mesh segmentation device according to claim 12, wherein the processor displays a first plane that comprises the first indication line and the third indication line with a first color, and displays a second plane that comprises the second indication line and the third indication line with a second color.

14. The digital dental mesh segmentation device according to claim 13, wherein the first plane and the second plane are translucent.

* * * * *